US00PP24481P2

(12) United States Plant Patent
Cho

(10) Patent No.: US PP24,481 P2
(45) Date of Patent: May 20, 2014

(54) ***COLOCASIA* PLANT NAMED 'WHITE LAVA'**

(50) Latin Name: *Colocasia esculenta*
Varietal Denomination: WHITE LAVA

(71) Applicant: John J. Cho, Paia, HI (US)

(72) Inventor: John J. Cho, Paia, HI (US)

( * ) Notice: Subject to any disclaimer, the term of this patent is extended or adjusted under 35 U.S.C. 154(b) by 0 days.

(21) Appl. No.: 13/815,951

(22) Filed: Mar. 16, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

PP22,420 P2 * 12/2011 Cho ..... Plt./373

OTHER PUBLICATIONS

Plant Delights (http://www.plantdelights.com/Colocasia-esculenta-White-Lava-PPAF-White-Lava-Elephant-Ear/productinfo/2867/.*

* cited by examiner

*Primary Examiner* — Anne Grunberg
*Assistant Examiner* — Keith Robinson
(74) *Attorney, Agent, or Firm* — James M. Weatherly; Cochran Freund & Young, LLC

(57) ABSTRACT

A new cultivar of *Colocasia* plant named 'WHITE LAVA' that is characterized by sagittate leaves which are semi-glossy medium green in color with bold cream markings and veins. The leaves of 'WHITE LAVA' are borne on glossy burgundy-red colored petioles. 'WHITE LAVA' grows with a compact and clumping habit. In combination these characteristics distinguish 'WHITE LAVA' from all other varieties of *Colocasia* known to the inventor.

4 Drawing Sheets

Genus: *Colocasia.*
Species: *esculenta.*
Denomination: 'WHITE LAVA'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'WHITE LAVA'.

*Colocasia* is a tuberous rooted perennial which is native to tropical Asia and Polynesia. It grows to 1.5-2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'WHITE LAVA' is the product of a formal breeding program carried out in a cultivated area in Kula, Hi. The purpose of the breeding program is to develop new commercial varieties by combining attributes not found in currently commercially available varieties.

'WHITE LAVA' is a seedling selection from the controlled pollination between the female parent breeding line '2007A-4' (unpatented) and male parent breeding line '2007A-51' (unpatented). Initially designated as '2008-66', 'WHITE LAVA' was derived as a single plant selected in 2008.

The new variety 'WHITE LAVA' exhibits medium glossy green leaves with flamboyant white markings and veins and slightly undulating leaf margins. 'WHITE LAVA' produces glossy red colored petioles.

'WHITE LAVA' may be compared to its parents as follows: The leaves are ⅓ to ½ times larger than its male parent and 2 to 3 times larger than its female parent. The male parent, '2007A-51', exhibits chartreuse colored leaves with a glossy finish with white markings and veins, a smooth margin, and light purple venation. The petioles are green in color with a matte finish. The female parent, '2007A-4' exhibits glossy green leaves with white markings and a purple spot on the upper leaf surface at the point of leaf and petiole attachment and an undulating margin. The petioles are a red burgundy color. In these aspects, this new variety differs from its parents.

The closest comparison variety in commerce known to the inventor is 'Nancy's Revenge' (unpatented). WHITE LAVA may be compared with 'Nancy's Revenge' as follows: Whereas 'WHITE LAVA' produces semi-glossy medium glossy green leaves with bold white markings and veins, the leaves of 'Nancy's Revenge' exhibit mainly central markings that do not extend to the veins. Whereas 'WHITE LAVA' produces glossy red petioles 'Nancy's Revenge' has green petioles.

The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation". Asexual propagation by "huli propagation" of 'WHITE LAVA' began in 2008 in Paia, Hi. by the inventor. Evaluation in field and pot studies have shown the unique features of 'WHITE LAVA' to be stable, uniform, and reproduces true to type in successive generations of asexual propagation.

SUMMARY OF THE INVENTION

The following traits have been repeatedly observed and represent the distinguishing characteristics of the new *Colocasia* variety named 'WHITE LAVA'. In combination these traits set 'WHITE LAVA' apart from all other varieties of *Colocasia* known to the inventor. 'WHITE LAVA' has not been tested under all possible conditions and phenotypic differences may be observed with variations in environmental, climatic and cultural conditions, however, without any variance in genotype:

1. 'WHITE LAVA' exhibits large sagittate leaves with slightly undulating margins.
2. The leaves of 'WHITE LAVA' are semi-glossy medium green in color with bold cream veins and adjacent tissue.
3. The leaves of 'WHITE LAVA' are borne on glossy burgundy-red colored petioles.
4. 'WHITE LAVA' grows with a compact and clumping habit'.

BRIEF DESCRIPTION OF THE DRAWINGS

The accompanying color drawings

Figure 1:
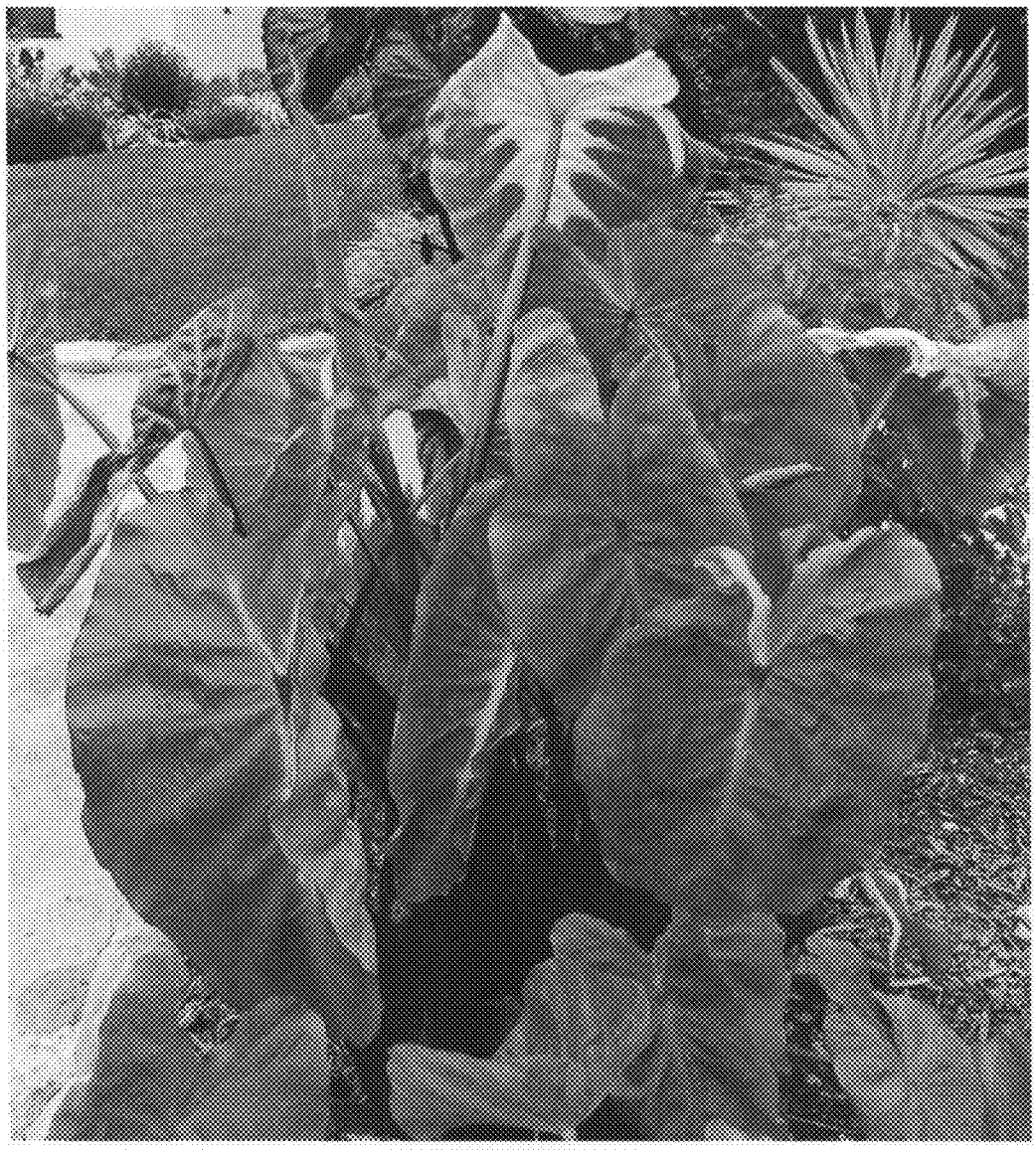
FIGS. 1 to 4 illustrate the overall appearance of 'WHITE LAVA' showing the colors as true as it is reasonably possible to obtain in colored reproductions of this type. Colors in the drawing may differ from the color values cited in the detailed botanical description, which accurately describe the actual colors of the new variety 'WHITE LAVA'.

The drawing labeled as FIG. 1 shows a mature plant of 'WHITE LAVA' grown out of doors in Santa Barbara, Calif.

Figure 2:
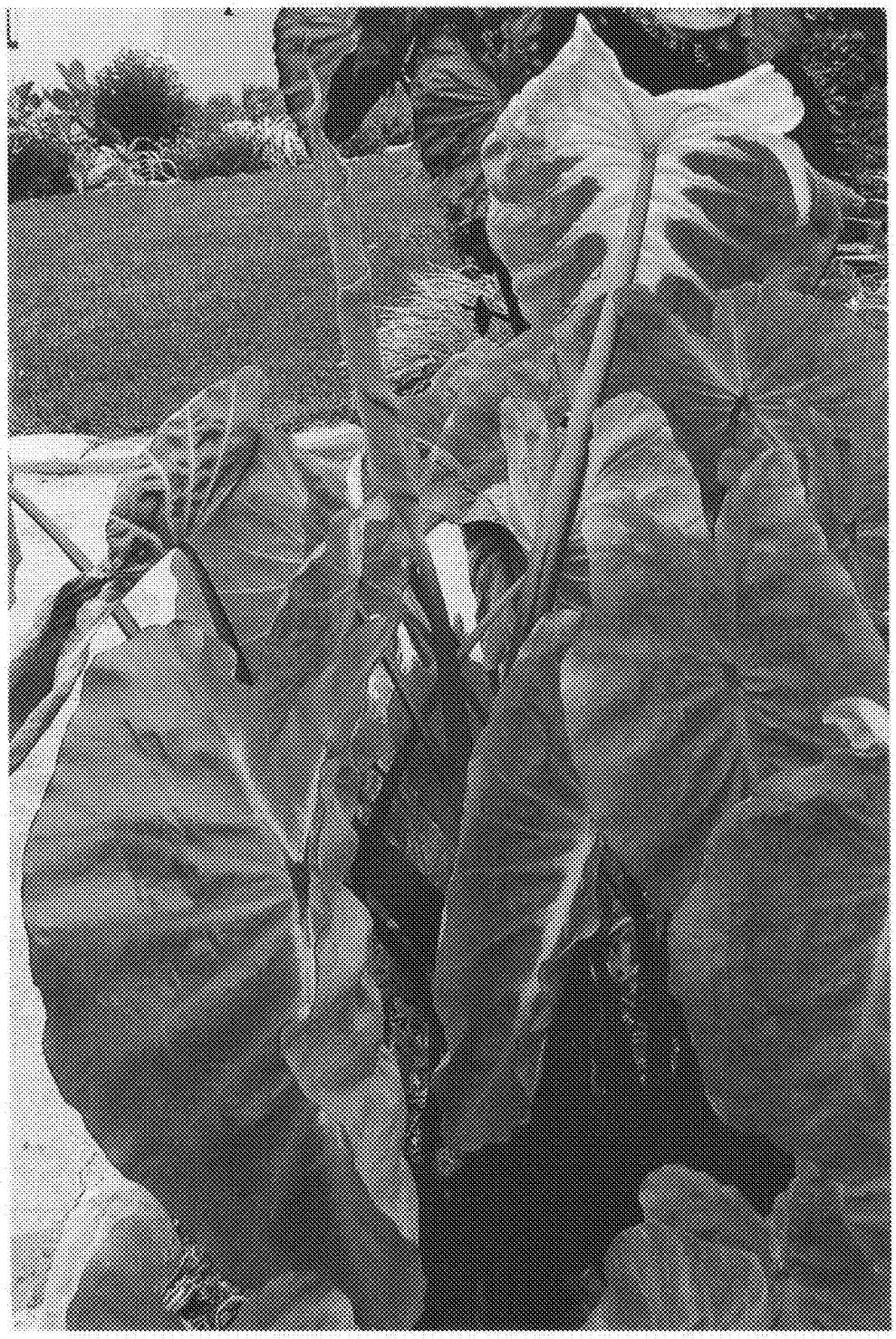

The drawing labeled as FIG. 2 shows a close-up of the petioles of 'WHITE LAVA'.

Figure 3:
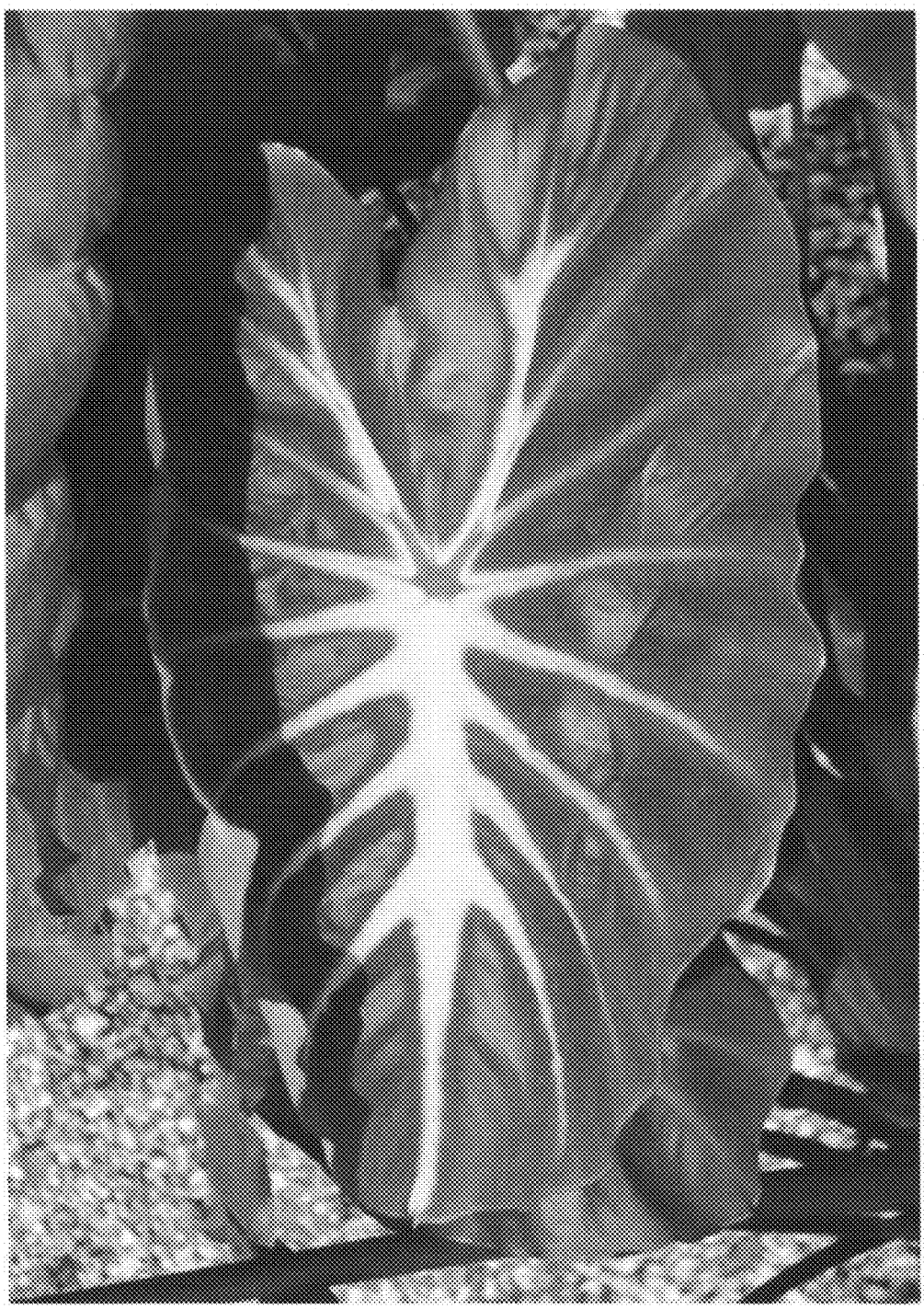

The drawing labeled FIG. 3 illustrates the upper surface of a fully expanded mature leaf of 'WHITE LAVA'.

Figure 4:
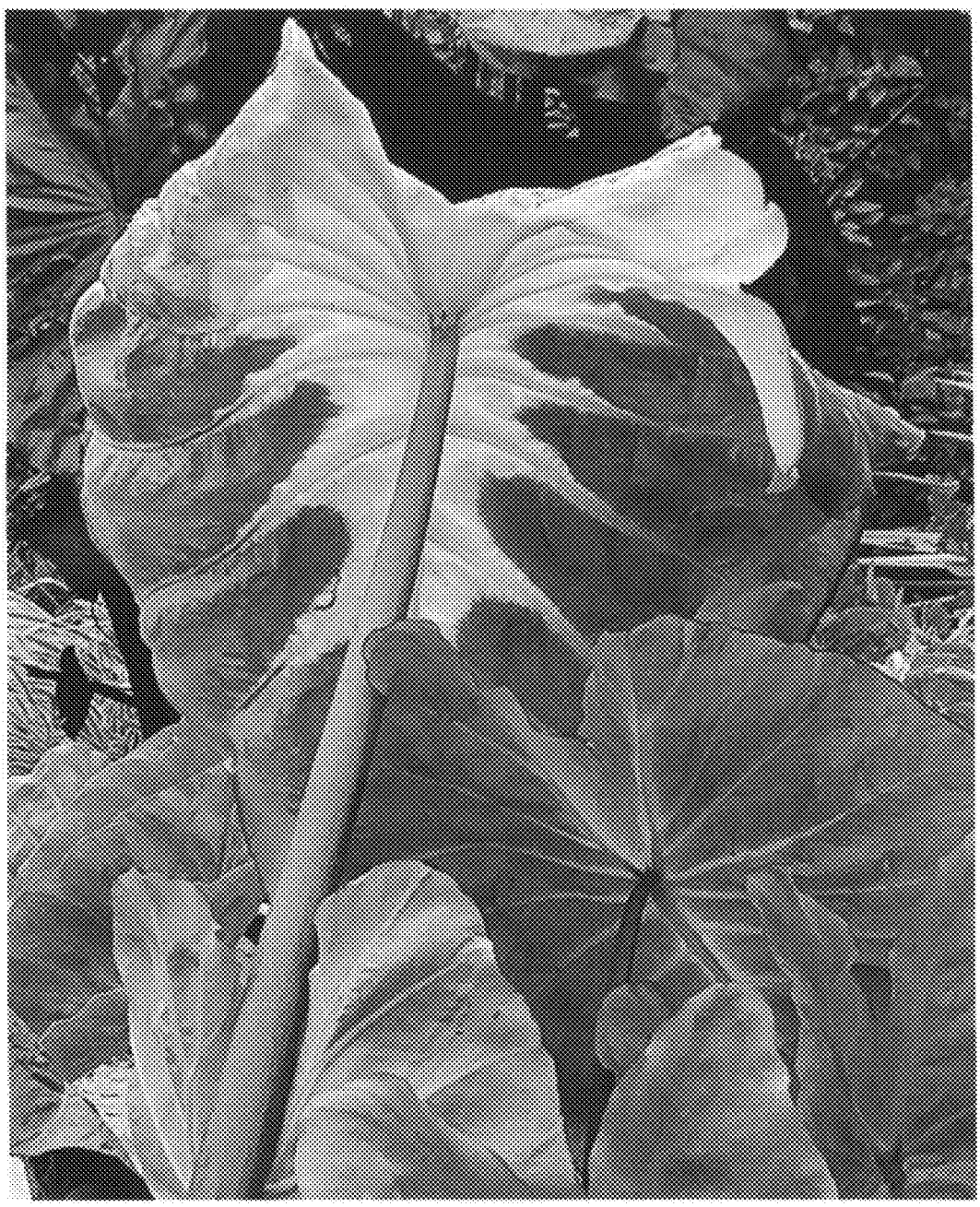

The drawing labeled as FIG. 4 shows the underside of a mature leaf of 'WHITE LAVA'.

All drawings have been made from a plant which is approximately 12 months old from a tissue culture division, and which has been grown out-of-doors in Santa Barbara, Calif. No growth regulators have been applied.

BOTANICAL DESCRIPTION OF THE PLANT

The following is a detailed description of the new *Colocasia* plant named 'WHITE LAVA'. Data was collected from a plant which was 12 months old from a tissue culture division, and which had been grown outside in Santa Barbara, Calif. The color determinations are in accordance with the 2007 edition of The Royal Horticultural Society Colour Chart, London, England, except where general color terms of ordinary dictionary significance are used. The growing requirements are similar to other *Colocasia*.

Botanical classification:

Genus: *Colocasia*.

Species: *esculenta*.

Denomination: WHITE LAVA.

Common name: Taro or elephant ears

Plant use: Container or landscape plant.

Cultural requirements: Cultural requirements are well draining soil or growing media, full sun to partial shade.

Root system: Tuberous.

Tuberous roots:

*Dimensions*.—18-20 cm in length, 8-10 cm in diameter.

*Color*.—155B.

Plant vigor: Vigorous.

Plant growth habit: Upright, non-spreading.

Plant growth rate: A one gallon container plant may be produced in 12-16 weeks from a 4 cm cell transplant.

Parentage:

*Female parent*.—2007A-4.

*Male parent*.—2007A-51.

Plant description: The plant has 4-6 suckers closely attached to the mother plant. A "mother plant" is the plant material which is first introduced into the soil to begin production. Typically, this plant material contains part of the huli and 2-3 leaf blades. This produces a "mother corm" which produces lateral shoots called 'cormels' which give rise to daughter plants. Daughter plants begin to appear above soil level about 2-3 months after planting of the mother plant.

Plant dimensions: 90 cm to 100 cm in height and 90 cm to 100 cm in width.

Plant hardiness: USDA Zone 7b.

Propagation: Propagation is accomplished by huli propagation and by tissue culture.

Time to develop daughter plants: Appear above soil around 2-3 months after planting.

Crop time: 1.5 to 2.5 months.

Pest or disease susceptibility and resistance: No more or less susceptible to disease or pests than other cultivars.

Foliage:

*Number*.—On average, a 5 to 6 month old mother plant maintains 5 functional leaves at a time; each new leaf is produced approximately every 10 days until the corm matures.

*Petioles*.—Length: 60-70 cm in length. Width: 8 mm (just below attachment to lamina), 18 mm (at the upper sinus), 25 mm (at the middle of the sinus). Color: N79B. Sap color: Colorless.

*Leaf*.—Dimensions at maturity: 40-45 cm in length and 30-35 cm in width. Average leaf sinus depth: 10 cm. Aspect: Erect with apex down. Shape: Sagittate lamina. Attitude: Oblique.

*Margins*.—Entire, slightly undulating.

*Margin color*.—1-2 mm marginal band N79B (both surfaces).

*Apex*.—Acuminate.

*Base*.—Peltate.

*Attachment*.—Petiolate with characteristic tissue formed at junction of leaf blade with the upper termination of the petiole. This area of the leaf tissue is also known as the "piko" and is evident by virtue of its upper surface color being similar to the color of the petiole and contrasting with the leaf color. The principal veins radiate from the piko.

*Piko color*.—60B becoming N77D as coloration extends up to 4 cm along upper pair of principal veins and 0.5 cm along midrib and along second, third and fourth pairs of secondary veins.

*Leaf sheath*.—Open.

*Texture*.—Matte (both surfaces).

*Leaf appearance*.—Semi-glossy mid-green with prominent variegation arising from cream-yellow principal and secondary veins whose color "bleeds" into adjacent leaf tissue.

*Leaf color* (*adaxial surface*).—141B becoming 144A towards margin, except veins and adjacent tissue 5D.

*Leaf color* (*abaxial surface*).—147C, except veins and adjacent tissue ranging between 2D and 5D.

*Veins*.—Palmate. Three principal veins radiating from the piko: one midrib extending 27 cm from the piko to the leaf apex, and one pair of veins extending towards each of the basal lobe margins. Up to eight pairs of secondary veins radiating from the region of the piko and from the midrib.

*Vein color* (*adaxial surface*).—Midrib entirely 5D, secondary veins 5D extending to 3 cm to 5 cm from margin, in which zone vein color is 146D.

*Vein color* (*abaxial surface*).—Midrib entirely 2D, secondary veins 5D extending to 3 cm to 5 cm from margin, in which zone vein color ranges between N77B and N77D.

Flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 105 mm to 120 mm long, with female flowers at the base, male flowers towards the tip, and sterile flowers in between, in the region compressed by the neck of the spathe. The extreme tip or appendage of the spadix has no flowers at all. The spathe is a large yellowish bract, 240 mm to 330 mm long, which sheathes the spadix. The lower part of the spathe is green (144C) in color and wraps tightly around the spadix and completely occludes the female flowers from view. The top portion of the spathe is yellow (13B) in color and is rolled inward at the apex, but is open on one side to reveal the male flowers on the spadix. The top and bottom portions of the spadix are separated by a narrow neck region, corresponding to the region of the sterile flowers on the spadix.

Seed: Seed is not produced naturally since male and female flowers within each inflorescence do not mature at the same time. Pollination can be achieved manually or in nature, only with the presence of small insect pollinators which are found in regions of genetic origin of the species, and not Hawaii.

The invention claimed is:

1. A new and distinct cultivar of *Colocasia* plant named 'White Lava' as described and illustrated herein.

* * * * *